United States Patent [19]

Ylikoski et al.

[11] Patent Number: 5,256,535
[45] Date of Patent: Oct. 26, 1993

[54] HYBRIDIZATION ASSAY AND MEANS TO BE USED IN THE ASSAY

[76] Inventors: Jyrki Ylikoski, Paimalantie 11, SF-20380 Turku; Pertti Hurskainen, Kuikankatu 15 A 20, SF-20760 Piispanristi; Patrik Dahlén, Rakuunatie 62 I 90, SF-20720 Turku; Christian Sund, Rieskalähteentie 33, SF-20300 Turku; Timo Lövgren, Valtaojantie 34, SF-20810 Turku; Marek Kwjatkowski, Hämeenkatu 14 C 54, SF-20500 Turku, all of Finland

[21] Appl. No.: 207,159

[22] PCT Filed: Oct. 16, 1987

[86] PCT No.: PCT/SE87/00474
§ 371 Date: Jun. 16, 1988
§ 102(e) Date: Jun. 16, 1988

[87] PCT Pub. No.: WO88/02784
PCT Pub. Date: Apr. 21, 1988

[30] Foreign Application Priority Data

Oct. 17, 1986 [SE] Sweden ................. 8604436

[51] Int. Cl.$^5$ ............... C12Q 1/68; G01N 33/20; G01N 33/533
[52] U.S. Cl. ............................ 435/6; 436/82; 436/546
[58] Field of Search ............ 436/546, 82; 435/6

[56] References Cited

U.S. PATENT DOCUMENTS

| | | | |
|---|---|---|---|
| 4,259,313 | 3/1981 | Frank I | 436/531 |
| 4,283,382 | 8/1981 | Frank II | 436/533 |
| 4,670,379 | 6/1987 | Miller | 435/6 |
| 4,707,440 | 11/1987 | Stravianopoulos | 435/6 |
| 4,795,700 | 1/1989 | Dervan et al. | 435/5 |
| 4,801,504 | 1/1989 | Burdick | 436/529 |
| 4,996,142 | 2/1991 | Al-Hakim et al. | 435/6 |

FOREIGN PATENT DOCUMENTS

| | | |
|---|---|---|
| 2963 | 7/1979 | European Pat. Off. . |
| 0077671 | 4/1983 | European Pat. Off. . |
| 77671 | 4/1983 | European Pat. Off. . |
| 0097373 | 1/1984 | European Pat. Off. . |
| 84/03698 | 9/1984 | European Pat. Off. . |
| 180492 | 5/1986 | European Pat. Off. . |
| 187332 | 7/1986 | European Pat. Off. . |
| 195624 | 9/1986 | European Pat. Off. . |
| 212951 | 3/1987 | European Pat. Off. . |
| 8403698 | 9/1984 | World Int. Prop. O. . |
| 87/02708 | 5/1987 | World Int. Prop. O. . |

OTHER PUBLICATIONS

Richardson "Terbium (III) and Europium (III) Ions as Luminescent Probes" Chem. Rev. 1982 vol. 82, pp. 541–552.

Nucleic Acid Research vol. 2, pp. 1017–1028, published 1986 (Syvanen A–C et al) "Time-resolved fluormetry: a sensitive method to quantify DNA-hybrids".

*Primary Examiner*—Robert A. Wax
*Assistant Examiner*—Hyosuk Kim
*Attorney, Agent, or Firm*—Lowe, Price, LeBlanc & Becker

[57] ABSTRACT

A method for the detection of a nucleotide sequence of a nucleic acid in a sample. The method comprises the steps: (i) contacting under hybridization condition the single stranded form of the nucleotide sequence with a single stranded nucleic acid probe, in which plurality of rare earth metal chelate groups is covalently linked via a water-soluble polymer of non-nucleic acid structure to a nucleotide acid that as one of its strand has the nucleotide sequence to be detected and as the other strand the nucleotide sequence of the probe, and (ii) detecting the formation of double stranded nucleic acid. The plurality of rare earth metal chelate groups have at least one metal ion selected from the group consisting of $Eu^{3+}$, $Sm^{3+}$, $Tb^{3+}$ and $Dy^{3+}$ as the chelated rare earth metal. The probes as given above are also claimed.

9 Claims, No Drawings

HYBRIDIZATION ASSAY AND MEANS TO BE USED IN THE ASSAY

BACKGROUND OF THE INVENTION

This invention relates to a hybridization assay utilizing nucleic acid probes labelled with lanthanide chelates that show time-delayed fluorescence.

Labelled nucleic acids have become indispensable in hybridization assays, performed both in vitro and, as in hybridocytochemical microscopy, also in vivo. Appropriate labelling of nucleic acids is a crucial point in their sequencing and applications may also be found in the different methodologies of nucleic acid separation. Nowadays, most of the efforts to find more sensitive markers have been made in the field of hybridization probes for the detection of specific, complementary nucleic acid sequences. This is natural in view of the great importance of such assays in medicine and molecular biology.

DNA or RNA can be labelled in a variety of ways. Generally, all labels may be detected directly i.e. the label, which is bonded to the nucleic acid is itself detectable, or indirectly when the label participates in one or more reactions thus generating detectable products.

DESCRIPTION OF PRIOR ART

Several new labelling methodologies have recently become available. Despite of many differences they can be systematized on the basis of some main criteria. In nucleic acid technology a common name for different labels is reporter group.

1. Methods of DNA Detection a) Direct detection method: Nucleic acids are commonly labelled with the radioisotopes $^{32}P$, $^{125}I$, $^{3}H$ or fluorescent markers. Especially in routine analyses the radioactive material tends to be replaced by the non-radioactive labels because of the serious drawbacks associated with the use of radioactive labels. Safety and disposal problems are obvious, but the low stability of materials with high specific activity together with their high cost should not be forgotten either.

Theoretically, fluorescent compounds are ideally suited to replace radioactive isotopes. To date the only examples of such fluorescent markers used in DNA labelling are fluorescein, rhodamine, Texas Red and NBD. The calculated high sensitivity which could be achieved using this type of reagents is, however, to a great extent limited by the fact that most biological samples including proteins also fluoresce thus bringing the background to a not always acceptable level to distinguish between the fluorescent marker and the protein.

b) Indirect detection method: Nucleic acids are labelled with different proteins possessing enzymatic activities e.g. alkaline phosphatase or horse radish peroxidase. The subsequent reaction of the appropriate substrate catalyzed by the attached enzyme usually generates an easy-to-detect colored product. It is constantly emphasized that an advantage of such a system is the fact that there is no need for a detecting apparatus, but this fact can also be seen as a disadvantage since this visual technique is not well-suited to quantitative analysis.

2. Attachment of a Detectable Group to DNA or RNA

The way in which report groups are linked to nucleic acids may serve as another criteria of differentiating between labelling techniques.

Direct attachment means that a detectable marker is bound to a nucleic acid already before a particular analytical process takes place. The label may be coupled to the nucleic acid enzymatically as in radiolabelling, by using DNA kinase and $\tau$ $^{32}P$ ATP, or by employing different $\sigma$ $^{32}P$ nucleoside triphosphates in the nick translation process. A properly activated label which is able to react with any existing or created function in nucleic acids, can also be chemically attached to nucleic acids.

Indirect attachment of the detectable group to nucleic acids can be realized by several methods. Among the most commonly used methods is the labelling of nucleic acids with a hapten, thus rendering them detectable by immunological means.

Examples of haptens useful in indirect attachment are fluorescein and a trinitrophenyl group (TNP). Antibodies with high affinity to these haptens have been well-studied and are easily obtainable. However, the complexity of nucleic acid derivatization together with a rather complex system of detection, problems in purification of some of the compounds, and quite a low sensitivity of the assay, make this technique rather unattractive.

N-acetoxy-N-2-acetaminofluorence (AAF) has been used for the chemical modification of nucleic acids for sensitive, colorimetric detection of target DNA using specific antibodies and peroxidase or alkaline phosphatase second antibody conjugates.

However, in view of the strong carcinogenic properties of AAF, other types of labels have been tried. For example biotin has been attached chemically to deoxyribonucleo-tides and these nucleotides were introduced into DNA by nick translation. A single stranded portion of biotin-DNA thus has been used as a hybridization probe. To detect double stranded DNA having biotin or hapten bound to one of its strands avidin or anti-hapten antibodies have been used. The DNA or protein is either labelled (e.g. by fluorescence markers) or detected by typical immunological methods.

The laborious procedure for the derivatization of DNA with biotin has been simplified by introducing a photo-activatable analog of biotin for the labelling of nucleic acids. However, the number of biotin groups which can be introduced to the DNA molecule, is limited in both the biotin and biotin analog methods. It has been found that the biotin technique is extremely difficult to carry out successfully and the results obtained are quite varied. The method is therefore extremely unreliable and does not provide any basis for routine polynucleotide sequence detection. Therefore, the approach of cross-linking biotin labelled histone to single stranded nucleic acids with glutaraldehyde, was useful. However, despite the possibility of a substantial increase in the biotin content, the sensitivity of assay was not sufficiently high.

Some General Remarks on Known Labelling Techniques

It is obvious that in the design of hybridization probes all labelling methods based on random derivatization of the exocyclic amino function in nucleic acids with an appropriate label must employ polydeoxy nucleic acid.

A short DNA sequence, for example an oligo nucleotide, is too sensitive for such an operation if effective further hybridization is expected. When using a long DNA probe the hybridization temperature has to be relatively high unless special additives (e.g. a high concentration of DMF) are present in the test mixture. Such high temperatures may limit the use of some enzymes as detectable markers by decreasing their activity. Moreover, it is well known that the longer DNA sequence requires a much longer time for hybridization to proceed, a fact which seriously limits the speed of assay without giving a proportionally equal increase in sensitivity.

In the literature there are only few reports of employing oligodeoxynucleotides labelled with non-radioactive markers for use as hybridization probes. The use of an octadecamer selectively monobiotinylated at the 5' position has proven unsuccessful as the sensitivity of the assay was far too low.

It is therefore commonly accepted that of all methods making use of indirect labelling or indirect detectable markers, the preferred procedure involves amplification of the signal. This is laborious, increases errors of method and makes routine analyses very difficult.

Polymeric substances of the non-nucleotide type have been employed in the design of non-radioactive hybridization probes. Biotin-labelled histone has been cross-linked to single-stranded nucleic acids with glutaraldehyde. The detection of target DNA with these probes and avidine-peroxidase conjugates was less sensitive than with radioactive methods. In another strategy, peroxidase or alkaline phosphatase was cross-linked to a polyethylene-imine of low molecular weight with p-benzoquinone and the resulting conjugates were cross-linked to DNA with glutaraldehyde. In both cases the polymers were used primarily as linkers between the DNA probe and the detectable units. It is therefore important to emphasize that in the present hybridization assay the main object of using a polymeric matrix is to amplify the detectable signal thus making the assay more sensitive. The polymeric matrix is not used as a simple linker molecule.

Hybridization assays employing rare earth chelates have been described before our priority date (EP-A-97,373; Syvänen et al., Nucl Acids Res 14(1986) 1017-27; and Hurskainen et al., In: NOMBA Nordforsk Symposium Gene Technology in Basic and Applied Research (Abstr.) Savonalinna, Finland, May 27-29, 1984, 12). Further details of other hybridization assays have been given during the priority year (WO-A-87/02708; and EP-A-212,951).

A survey of the literature in this area clearly shows that when the aim is to design an easy, reliable and sensitive hybridization method, it is desirable to use directly labelled and detectable probes. This is in contrast to sandwich techniques, when amplification of signal is desired it is generally realized by increased label density. A hybridization assay method of choice should not involve either radioactive isotopes or highly toxic intermediates.

The Invention

The present invention provides an improved hybridization assay method utilizing certain labelled nucleic acid probes. It is a method for the detection of a nucleotide sequence of a nucleic acid in a sample. The method has the following major characteristic steps:

(i) Contacting under hybridization condition the single stranded form of the nucleotide sequence present in a sample with a single stranded nucleic acid probe, so as to form a double stranded nucleic acid which has as one of its strands the nucleotide sequence to be detected and as the other of its strands the nucleotide sequence of the probe. The probe has as one part, a nucleotide sequence that is complementary to the sequence to be determined, and as the other, a plurality of rare earth metal chelate groups that ar covalently linked, via a water-soluble polymer of non-nucleic acid structure, to its nucleotide sequence. One probe can contain many sequences complementary to the one to be determined and/or of pluralities of rare earth metal chelate groups.

(ii) Determining or detecting the double stranded nucleic acid so formed by using time-resolved spectrofluorometry to measure the rare earth metal chelate incorporated into the double stranded nucleic acid.

The plurality of rare earth metal chelate groups has at least one metal ion selected from the group consisting of $Eu^{3+}$, $Sm^{3+}$, $Tb^{3+}$ and $Dy^{3+}$, and is preferably europium and terbium ions. The intensity of fluorescence emitted from the double stranded nucleic acid is a quantitative measure of the nucleotide sequence to be determined. The use of a covalently bound polymeric group carrying several rare earth metal chelate groups amplifies the signal from the probe. A brief calculation of the fluorescence intensity using a probe labelled with only a few fluorescent markers showed that the sensitivity of such an assay will be insufficient. This realization is especially applicable to the detection of viral DNA in the early stages of infection. Therefore, the important feature in the invention is the use of water soluble polymeric compounds as a matrix to which a large number of europium or terbium chelates are covalently coupled. This covalent coupling gives a large amplification of the detectable signal. Contrary to many existing methodologies, the present hybridization assay is a straightforward, direct, and one-step procedure.

One important aspect of the invention is the particular probes that are described in this specification and that are used in the assay of the invention. For practical considerations as shown in the examples, the chelated lanthanide ion always non-radioactive.

Hybridization Assays

Hybridization assays are well-known in the art. As in common immunoassay techniques, the hybridization assays can be divided into two groups including homogeneous assays and heterogenous assays. The homogenous hybridization assays utilize labels that in one way or the other change their signal as a consequence of being incorporated into double stranded forms of DNA. Accordingly no separation of single stranded nucleic acids from double stranded nucleic acids is required in the homogenous assay variants (see for instance EP-A-144,914 and EP-A-70,685). In the heterogenous assays, separation of double stranded DNA containing the probe from unhybridized probe is accomplished by the use of a matrix which is insoluble in the assay medium and which selectively is able to bind either the double stranded DNA or the unhybridized probe. The binding may be carried out as a biospecific absorption employing covalently bound oligonucleotide sequences or other biospecific affinity reactants. Isolubilized streptavidin or antibodies can specifically absorb nucleic acids equipped with biotinyl or homologous haptenic groups. (See for instance Dunn et al, Cell 12 (1977) 23-36; Ranki M et al., Gene 21 (1983) 77-85; Meinkoth and Wahl, Anal Biochem 138 (1984) 267-84; Syvänen et al., Nucl Acids-Res 14 (1986) 5037-48; Dattagupta and Crothers, EP-A-130,523; WO-A-85/02628 and U.S. Pat. No. 4,563,419). The most popular heterogenous method at present time is hybridization on filter paper, e.g. nitro cellulose paper. In this hybridization assay method the single stranded DNA to be assayed is adsorbed to the filter paper, and thereafter the filter paper is saturated with DNA non-homologous to the DNA to be assayed and contacted under hybridization conditions with the DNA probe.

The conditions required to accomplish hybridization depend on the probe length, i.e. the length of the oligonucleotide sequence to be hybridized, and the specificity desired. As a general rule, longer nucleotide sequences that are complementary require a longer time for hybridization to occur. An increase in temperature and/or special additives, such as DMF, may produce more rapid reactions. Normally the hybridization solutions are buffered to pH values of 5-9 and the hybridization are carried out at constant temperatures, 18°-65° C. for 3-48 hours. For homogenous variant hybridization assays it is very critical not to add to the hybridization media, chemicals which negatively influence the signal emitted by the label(s).

The Polymer and Its Derivatization

The water-soluble polymer used in the present hybridization assay is of non-nucleic acid structure, and may be a biopolymer or a synthetic polymer. Derivatized forms of biopolymers may also be used. When not bound to a nucleic acid, the polymer should exhibit a plurality of functional groups allowing covalent attachment to a nucleic acid. Thus the most suitable polymers have more than 10, such as more than 50 OH-groups or amino groups. The OH-groups may be part of a carboxylic acid group or an alcoholic or phenolic hydroxyl group. The polymer can have molecular weights above 1,000 daltons, and preferably molecular weights above 5,000 daltons. In most cases the polymer has a molecular weight below $10^6$ daltons.

Linear or substantially linear polymers are preferred because they will have a favorable geometry in relation to the hybrids formed. Another obvious demand placed on such polymers is their solubility in water. Free water solubility of the polymer chelate derivatives, as well as water solubility of the final lanthanide chelate-polymer-DNA complex are imperative.

The first successful attempt to synthesize the derived polymers of the invention was made by condensation of polyacids with chelates possessing a free amino group. A water soluble carbodiimide was used as the coupling reagent. Next, since most of the chelates available were best suited for derivatization of free, preferably primary, amino groups with relatively high pKa (optimum region pKa 8-11), polymers which meet such functional requirements were directly tested. Other polymers of interest were prepared by appropriate derivatization, introducing free amino functions to the polymers which lacked them from the beginning.

Particularly good coupling results were obtained with the following polymers: polysaccharides, such as chemically modified dextrane, polyvinylamine (PV.A), polyethyleneimine (PEA), polylysine (PL), chemically modified polyacrylamide, carboxymetylated polyvinylamine (CM PVA) and polyacrylic acid. Two of these, polyethyleneimine and dextrane, do not fully meet the criterion of linearity. Nevertheless, both compounds consist of long intervals within which the required linear geometry is preserved and accordingly are substantially linear. All these polymers are readily dissolved in water at all derivative stages.

Polyvinylamine was prepared according to a known method, and stored in a convenient form of hydrochloride as dry powder. This material ($M^{PS}$ $3.4 \times 10^4$) has been used as a matrix for the synthesis of polymeric water soluble dyes and has been shown to be the best alternative because of its high reactivity. It has the highest density of the groups which can be derivatized. Polyethylene-imine used in our experiments had an average molecular weight of $5 \times 10^4$ to $6 \times 10^4$, $1,5 \times 10^4$ to $3 \times 10^4$. Polylysine hydrobromides used had molecular weights of $3 \times 10^4$ to $7 \times 10^4$, respectively. Functionalized polyacrylamide was made from polyethylacrylate Mw 72,000. The synthesis is described in Example 1. The polyacrylic acid used had a Mw$\approx$5,000. The procedure for carboxymethylation of polyvinylamine is outlined as Example 2.

Polyacrylamide is an example of a desired compound which is prepared not by derivatization of already existing polymeric material but through the synthesis of a monomeric acrylamide chelate and its subsequent polymerization as in Example 3. Copolymerization of such monomers with other appropriate acrylamide derivatives will create products possessing all the necessary features like proper solubility, net charge, and the presence of other functional groups.

Theoretically, two different derivatization methods are possible for polymers possessing free amino functions. Derivatization with a lanthanide chelate followed by a derivatization with an appropriate bifunctional reagent, and coupling of an activated oligo-DNA or poly-DNA probe is the most economical derivatization method. Reverse order of the reactions is also possible using this method since the reactivity of the exocyclic amino function in DNA is very low, and thus no derivatization with chelate takes place on these amino functions. This has been verified in several blank reactions with DNA and the active forms of chelates.

For acidic polymers (polymers containing for instance carboxylic acid groups) only the first route, i.e. functionalization with a chelate, followed by reaction with a bifunctional coupling reagent and the addition of nucleic acid can be used.

Both in case of polyamines and polyacids polymers, the reaction cycle could be stopped at the level of an activated polychelate (Examples 4 and 5). Such functionalized polymers can be stored for long period of time and coupled with different DNA probes whenever necessary. This type of derivatization has therefore the advantage of being "universal".

Functionalization of acidic polymers is a very quick process, and the degree of condensation, performed in a water solution and employing a large excess of EDAC (water-soluble condensing agent), was directly proportional to the amount of used amino reagent.

The labelling of amino-functionalized polymers with chelates has been performed in aqueous media using a triethylammonium bicarbonate buffer, pH 10.

The use of a phosphate buffer should be avoided as it forms insoluble salts in water with polyamines. The extent of the derivatization can easily be manipulated by changing the pH or the chelate concentration. For instance, using two equivalents of isothiocyanato chelate per each amino group in PVA at pH 10, essentially all amino functions can be derivatized in an overnight reaction.

By performing this reaction at pH 7, only 35–50% of the amino groups were labelled. This was determined after standard gel filtration and counting of lanthanide fluorescence.

The Nucleic Acid Portion of the Probe

Two general alternatives exist in the choice of the nucleic acid portion of the probe.

The use of polynucleotides is often favorable when the nucleic acid is easily accessible and no data exists on the sequence of the target molecule. The probe can be prepared e.g. from a double-stranded DNA identical in sequence to two strands of the gene sequence to be detected. On denaturation of the double-stranded DNA, the two strands are hybridized to two strands of the gene sequence to be detected. The probing sequence of its double-stranded precursor can be produced by cloning it in a plasmid or a phage. Multiple labelling of such poly-DNA probes with polymeric lanthanide chelates will therefore be an attractive procedure making it possible to overcome the disadvantages connected with labelling and amplifying the signal as in cases where other non-radioactive markers are used.

The native molecule of a nucleic acid has to be modified by introducing groups which are able to selectively react with a bifunctional coupling reagent. An example of a group which fulfills these criteria is the thiol groups. Thiol groups which can be introduced by employing several existing procedures (Example 6). The procedure of Example 6 is rapid, reliable, safe and should allow inexpensive small or large scale labelling of any DNA with lanthanide chelates.

The already mentioned low reactivity of natural amino functions in DNA permits only slight cross-linking between DNA and polymeric chelates. This is necessary for persistence of the intact fragments in DNA which are vital features of efficient hybridization. Recently there is a tendency to employ short oligonucleotides instead of longer poly-DNA fragments as hybridization probes. This is especially important in the design of routine assays when time plays an important role. These small fragments with the sequence long enough to be specific for the sequence to be detected should contain at least 16 nucleotides. Such oligonucleotides can be easily synthesized by employing commercially available reagents and apparatus, even by non-chemists. An additional feature of synthetic DNA fragments is their specific and regioselective derivation in a protected state. One of these reactions is the recently published procedure for selective 5'-thiolation of synthetic oligonucleotides (Example 7). This procedure, in conjunction with the already existing procedures of specific terminal derivatization even in a fully deprotected state, together with simple preparative purification methods make them an alternative to the polydeoxynucleotide probes (Examples 8 and 9). Perhaps the greatest advantage using short DNA fragments becomes clear when considering the hybridization process.

Oligo DNA probes are characterized by their very favorable kinetics of hybridization which allow the assay to proceed at low temperature and in a much shorter time period than the temperature and time periods which are necessary for poly-DNA probes. This is of course, only true of relatively free oligo-DNA probes. The oligo DNA probes which are bound to globular molecules (e.g. proteins) may behave very differently and, in the most drastic case, can even totally lose their base pairing properties. Fortunately, however, the cross-linking of 5'-functionalized oligo-DNA probes to the linear polymers was successful without any detectable differences in hybridization efficiency as compared to free probes.

Rare Earth Chelates

Different types of functionalized rare earth chelates are known in the art. Some of them exhibit fluorescence when excited at the appropriate wave length. Others do not. The fluorescent property of rare earth chelates is not critical for their use in heterogenous hybridization assay variants of the present invention, because techniques have been developed that can transform non-fluorescent rare earth chelates to fluorescent ones. Hemmilä et al., Anal. Biochem. 137 (1984) 335–43). For homogenous hybridization assay variants, it is more critical that chelates having fluorescent properties be selected. It is thus more important to select chelates according to the stability that is required in the hybridization assay, than to have inherent fluorescent properties as the selection criteria.

In order to determine if a given chelate has the satisfactory stability for use in a hybridization assay, it should be tested in the assay to be run. If the sensitivity is satisfactory the chelate is of satisfactory stability. Suitable chelates to be used in the invention have carboxylate, phosphate or phosphonate anionic groups and/or primary, secondary or tertiary amino nitrogen atoms located in the molecule such that they simultaneously coordinate, via their negatively charges oxygen or nitrogen, respectively, to the rare earth metal ion so that more than three, preferably more than four, five- or six-membered rings are formed. This definition means that the chelates in question have more than four, preferably more than five heteroatoms selected among the above-mentioned nitrogens and oxygens, and that the rare earth metal ion is a joint member for all the rings. Nitrogens in aromatic rings are present as tertiary nitrogen atoms. Five-membered rings are preferred. This definition of a stable chelate can be found in common text-books and includes those given in the patent literature set forth below.

Different types of chelates that can be used in our invention have been described previously (EP-A-195, 413; EP-A-139,675; EP-A-68,875; EP-A-203,047; EP-A-171,978; EP-A-2,570,703; U.S. Pat Nos. 4,352,751 and 3,994,466). With respect to hybridization assays that require extremely harsh conditions we have developed a series of preferred chelates are represented in Example 10. They have as the common denominator a pyridine ring substituted at the 2 and 6 positions with groups that together with the pyridine nitrogen, can chelate a metal ion. To the pyridine ring is bound only hydrogens and/or aliphatic carbon atoms. These extremely stable chelates agree with the definition for stable chelates given in text-books.

The chelate employed in the present hybridization assay has to be sufficiently stable under assay process steps which requires harsh conditions, such as elevated temperatures (above 60° C.) and the presence of other chelating agents (EDTA etc.). To each linear polymer molecule may be bound more than 10, such as more than 25 chelating groups. The substitution degree with respect to the lanthanide chelate groups in the lanthanide chelate polymer is usually more than 20% and can in many cases exceed 50%.

EXAMPLE 1

Preparation of Amino Functionalized Polyacrylamide (Scheme 1)

2.0 g of polyethyl acrylate (M.w. 72000—Aldrich) was treated at 50° C. with 50 ml of dry ethylenediamine in a 100 ml round bottom flask using a slow speed magnetical stirrer. After 24 h stirring the mixture was evaporated to dryness on a rotavapor using an oil pump, and coevaporated three times with n-butanol. The residue after dissolving in 10 ml of methanol was acidified with 5 M HCl and again evaporated to dryness. The solid crude product was dissolved in water (20 ml) and precipitated from acetone. Elementary analysis of the material showed a minimum of 80% conversion of starting ester functions.

EXAMPLE 2

Preparation of Carboxymethylated Polyvinylamne (CMPVA) (Scheme 2)

1.0 g (12.6 mmole) of polyvinylamine hydrochloride (PVA HCl) was dissolved in 20 ml of water and the pH of solution was brought up to 10.5 by addition of 5 M NaOH. 10.5 g of bromocetic acid (75.6 mmole) dissolved in 20 ml of water and neutralized with NaOH was dropped into magnetically stirred PVA solution, maintaining pH 10.5 by addition of 5 M NaOH. After complete addition the mixture was left stirred overnight. The crude product was isolated by addition of 500 ml of ethanol. The white precipitate was separated, dissolved in water and dialyzed against distilled water.

EXAMPLE 3

Preparation of Functionalized Polychelates by the Polvmerization of Monomeric Units (Scheme 3 and 4)

A) Synthesis of acrylamido chelate (scheme 3). 100 mg of an amino functionalized lanthanide chelate (EP-A-139,675) was dissolved in 5 ml of 1 M trimethylammonium bicarbonate buffer pH 9.5 and cooled to 0° C. To this stirred solution 1.5 ml of acrylol chloride was injected in few portions. Progress of the reaction can be monitored on TLC using acetonitrile—$H_2O$ (4:1) as solvent. The mixture was stirred for 1 hr and evaporated to dryness on a rotavapor, followed by several coevaporations with water. The final residue was dissolved in a small amount of water and lyophilized in high vacuum.

AA) Analogously the chelates of example 10 (compounds 12) can be used.

B) Synthesis of Monoacylamido Derivative of Diaminoalkane—General Description (Scheme 4).

Monotrifluoroacetate of a $(\alpha,\omega)$ diaminoalkane was dissolved in dry pyridine: dichloromethane (1:1) and cooled to $-10°$ C. To the stirred mixture 1.5 ml acryloyl chloride was added. The mixture was stirred for 30 min. and partitioned between $CHCl_3$ and saturated $NaHCO_3$. The organic extracts were evaporated and coevaporated three times with toluene. The oily residue was dissolved in methanol (10 ml/mmole) and an equal volume of saturated $Na_2CO_3$ was added at once. The turbid mixture becomes clear after about 1 hr and the hydrolysis of the trifluoroacetamido group was virtually complete after 5 h. The reaction mixture was then evaporated to a small volume and extracted six times with $CHCl_3$/EtOH (1:1) addition of saturated $(NH_4)SO_4$. After evaporation the extract was purified by short column chromatography using $CHCl_3$/EtOH (6:4) as the final solvent. After evaporation of proper fractions the oily product was stored at $-20°$ C. after addition of a polymerization inhibitor.

C) Method for synthesis of functionalized polymeric chelates.

To a mixture consisting of acrylamido chelate (point A), functionalized acrylamide (point B), in a ratio of 2:1 and dissolved in phosphate buffer ($\mu=0.01$) pH 8.0, so that the concentration of acrylamido monomers was 5%, TEMED (5% aqueous solution) and ammonium persulfate (5% aqueous solution) were added to achieve a final concentration of 0.047% (TEMED) and 0.033% (ammonium persulfate). The mixture was kept at 50° C. for 30 min, and the polymer was separated from low molecular weight components by gel chromatography.

Using this method, polymers with chelate functions at up to 60% of its amido groups can be easily obtained. Including other acryl monomers (e.g. acrylated amino acids or acrylated taurine) and varying the ratios of added monomers allows for polymers of different constitution to be synthesized.

CC) By using the acrylamido chelate of step AA, other functionalized polyacrylamides containing the corresponding chelate can be obtained.

EXAMPLE 4

Application of Carboxymethylated Polyvinylamine (CMPVA) for the Synthesis of Activated Polymeric Chelate (Scheme 5)

5.85 mg (0.01 mmole) of $Eu^{3+}$ chelate in amino form (same as in Example 3A) was dissolved in 50 $\mu l$ of water. To this solution a solution of 2.0 mg (0.02 mmole—based on carboxylate) carboxymethylated polyvinylamine in 30 $\mu l$ of water was added. Solid EDAC (38 mg—0.20 mmole) was then added in three portions during 1 hr, and the pH of the solution was maintained at 5.5 by addition of diluted HCl. To this reaction mixture of bifunctional reagent (see scheme 5), (0.32 mg—0.001 mmole), was added, followed by EDAC (19 mg—0.01 mmole). The mixture was incubated for 30 min, and the product was precipitated by addition of acetone. The solid, centrifuged material was dissolved in water and the polymeric product was separated by filtration through a Trisacryl column (2×50 cm) using 50 mM Tris-HCl, 0.5 NaCl buffer pH 7.0.

The determination of the europium content in pooled high molecular fractions established a 60% incorporation of the starting monomeric chelate, which corresponds approximately to 200 chelates per polymeric molecule. Finally, the material was dialyzed with water, precipitated from acetone and stored as a dry powder.

EXAMPLE 5

Application of Polyvinylamine for the Synthesis of Activated Polymeric Chelate (Scheme 6)

Step A. 500 $\mu g$ (6.3 $\mu mole$ based on amino function) of polyvinylamine hydrochloride, dissolved in 20 ml of $H_2O$, was labelled with 10 $\mu mole$ of an isothiocyanate functionalized lanthanide chelate (see EP-A-139,675 and compound 13 of Example 10) in the presence of 10 $\mu moles$ of triethylamine. The reaction mixture was incubated overnight at 20° C. The unreacted chelate was removed by gel filtration through a Sephadex ®

G-50 column (0.7×20 cm). Fractions containing lanthanide ions were pooled, desalted and concentrated. This procedure gave a polymer with a high degree (50–75%) of substitution.

Step B. The polymeric chelate (from Step A) was dissolved in 50 µl of phosphate buffer pH 6.5 and a bifunctional coupling reagent (see scheme 6), 270 micrograms (0.63 micromole) in 10 µl of ethanol, was added. The reaction mixture was incubated for 6 hr with occasional shaking. The product was isolated after filtration through a Sephadex ® G-50 column and precipitation from acetone.

EXAMPLE 6

Construction of Lanthanide Labelled Polydeoxyribonucleic Acid

Hybridization Assay Variant A:

10 µg of single-stranded phage M 13 mp 10 DNA containing an Adenovirus 2 Xba I restriction fragment (0–3.85 arbitrary units) of about 1350 bp is reacted with 150 µl of 25% glutardialdehyde and 50 µg of an europium-labelled PVA (from Example 5) in phosphate-buffered saline (10 mM Na—K-phosphate pH 7.4, 0.18 M sodium chloride). The reaction is allowed to proceed for 20 minutes at 37° C. After incubation the non-reacted aldehyde groups were blocked by reacting with 500 µl of 1 M lysine, pH 7.5 at 20° C. for one hour.

Hybridization Assay Variant B

Step A: 200 µg of single-stranded M 13 DNA containing a fragment of Adenovirus 2 DNA was modified with sodium bisulfite-ethylenediamine at pH 6.5 for 2 h according to published methodology. The dialyzed and concentrated sample was then dissolved in 1 ml of PBS (phosphate buffered saline) (pH 8.5). Solid S-acetylmercaptosuccinic anhydride (1 mg—5.75 µmole) was added and the reaction mixture was kept at room temperature (R.T.) for 60 min with occasional shaking. The mixture was made 0.3 M with respect to sodium acetate and 2.5 volumes of ethanol was added to precipitate DNA. The precipitate was dissolve din 1.0 ml of 0.01 M sodium hydroxide and kept for 60 min at R.T. for hydrolysis of S-acetyl protecting groups after which the mixture was made neutral with 0.1 M HCl. DNA was precipitated and purified from low-molecular weight compounds by gel chromatography through Sephadex ® G-25 (0.7 cm×15 cm) in 0.05 M phosphate buffer, pH 6.5.

Step B: 200 µg of the purified single-stranded DNA containing free sulphydryl groups and 500 µg of Eu-PVA from example 4 or example 5, step B, were mixed and incubated at room temperature for 20 hours. The Eu-PVA-DNA conjugate was purified by gel filtration through a Sephadex ® G-150 column (0.7 cm×47 cm). The column was equilibrated and eluted with PBS.

EXAMPLE 7

Construction of Lanthanide-Labelled Oligodeoxribonucleic Acid (Scheme 7)

Step A. A hexadecamer DNA probe was synthesized in large scale employing standard solution chemistry. The 5'-protecting group was then removed and the probe was labelled with a protected thiol function (S-Tr) according to the procedure of Connolly B.A., Nucl. Acids Res. 13 (1985) 4485–4502 modified by using phosphotriester chemistry, followed by standard deprotection and purification methods. Finally the S-Tr protecting group was removed with silver nitrate in buffered by sodium acetate system. The excess of silver was removed with hydrogen sulphide and the precipitated silver sulphide was filtered out with help of 2µ filters. The clear filtrate was concentrated and desalted on Sephadex ® G-25 (10×200 mm).

Step B. 1.0 mg of 5'-thiolated oligo DNA probe was mixed with activated PVA chelate (from Ex. 5) at pH 7.0 and in different ratios (3:1–20:1). All mixtures were incubated overnight and separated using a Sephadex G-100 column (0.7 cm×50 cm). The column was equilibrated and eluted with PBS.

EXAMPLE 8

Hybridization Using DNA Probe of Long Sequence

Step A: Adenovirus 2 DNA and PBR 322 as a control DNA were denatured and spotted onto nitrocellulose filters. Amounts of DNA from 100 ng down to 1 pg were applied. Filters were baked in a microwave oven for 3 minutes.

Step B: Filters obtained in Step A were prehybridized at 42° C. for 2 hours in 50% formamide containing 1 M NaCl, 1 mM EDTA, 10 mM Tris-HCl pH 7.0, 5×Denhardt's reagent Step C: After prehybridization the filters were transferred to a hybridization solution containing 50% formamide, 1 M NaCl 1 mM EDTA, 10 mM Tris-HCl, pH 7.0, 5×Denhardt's reagent, 0.5% sodium dodecyl sulphate (SDS) and 50 µg per ml of denatured herring sperm DNA. Eu-PVA-DNA conjugate (Examples 1, 2 and 3) was added to give the final probe a DNA concentration of 0.2 microgram/ml. The filters were hybridized at 42° C. for 4 hours. The filters were then washed at 42° C. with 0.15 M NaCl, 10 mM Tris-HCl pH 7.0 containing 0.5% SDS three times for 15 minutes.

Step D: The spots in the filters were punched and the time-delayed fluorescence from europium in each spot were measured using enhancement solution (Wallace Oy, Finland). Sensitivity of the test is 10 pg of Adenovirus 2 DNA. Values which are twice the mean of the negative controls or more were considered positive.

EXAMPLE 9

Hybridization Using Oligometer DNA Probe

Step A: As in example 8.

Step B: Filters were presoaked at 30° C. for an hour in 1 M NaCl, 1 mM EDTA, 10 mM Tris-HCl pH 7.0, 5×Denhardt's reagent and 50 µg per ml of denatures herring sperm DNA.

Step C: After prehybridization the filters were transferred to a hybridization solution containing 1 M NaCl, 1 mM EDTA, 10 mM Tris-HCl pH 7.0, 0.5% SDS, 5×Denhardt's reagent and 50 µg per ml of denatured herring sperm DNA. A Eu-PVA-hexadecamer conjugate from example 7, step B, was added to give a hexadecamer concentration of 20 ng/ml. Hybridization was carried our at 30° C. for 3 hr. The filters were washed in 1 M NaCl containing 10 mM Tris-HCl pH 7.0 and 0.5% SDS first at 30° C. for 15 minutes and then at 35° C. for 10 minutes.

Step D: Spots were punched and the europium in each spot was measured as in example 8, step D. A positive signal was detected when the spots in the filters contained 200 pg or more of Adenovirus 2 DNA.

EXAMPLE 10

Synthesis of Novel Functionalized Chelates

For a survey of the synthetic route employed and structures of the compounds involved see scheme 8.

NMR-spectra were recorded for the end product and intermediates synthesized and found to be in accordance with the structures given. The compound numbers refer to those given in scheme 8.

Compound 2: Liquid ammonia (150 ml) was introduced to a 250 ml three-necked round bottomed flask equipped with a mechanical stirrer, dropping funnel and outlet tube and immersed in a dry ice/ethanol bath. Sodium amide was generated by addition of 20 mg of iron nitrate ($Fe^{3+}$) followed by metallic sodium (2.09 g 0.09 mole). The deep blue solution was stirred for one hour and the solution of collidine (1) (10.06 g, 0.083 mole) in 20 ml of dry diethylether was introduced into the reaction—addition time 15 min. The formed yellow suspension was stirred for an additional 45 min followed by the addition of benzylchloride (6.33 g, 0.05 mole) dissolved in 10 ml of dry diethylether. The reaction mixture was stirred for 45 min and the excess of sodium amide was neutralized by addition of ammonium chloride (4.82 g, 0.09 mole) dissolved in 20 ml of $H_2O$. Ammonia was evaporated and the residue was partitioned between water and diethylether. The collected etheral phase was dried over sodium sulphate and evaporated. The brown residual oil was fractionated collecting a fraction distilling at 130° C./0.1 mmHg. Yield=6.17 g (55%), oil.

Compound 3: Compound (2) (20 g, 88.9 mmoles) was dissolved in THF (150 ml), and nitric acid (6.7 ml, 60% aq. solution, 1 eq) was added. Diethylether was added to the clear solution until it remained dimmy, and the mixture was left in the freezer for crystallization. The white crystals of nitrate (quantit. yield) were added in small portions to well-chilled sulphuric acid (150 ml) never allowing the temperature to reach 10° C., whereafter the mixture was warmed at 50° C. for 10 min. The resulting brown solution was poured onto ice and neutralized with solid sodium hydrogen carbonate. The organic material was extracted with chloroform (3×200 ml), and after drying over sodium sulphate, the chloroform extract was flash chromatographed using 4% ethanol/chloroform as a solvent. The appropriate fractions were collected and evaporated yielding a solvent. The appropriate fractions were collected and evaporated yielding a pure yellow solid. Yield: 22.82 g (95%).

Compound 4: Compound (3) (22.82 g, 84.5 mmole) was dissolved in chloroform (100 ml), and 16 g (94 mmole) of m-chloroperbenzoic acid (mCPBA) was added in small portions at RT over a period of 30 min. The mixture was stirred for an additional 2 h and after a negative TLC test for the starting material it was worked up by partitioning between sat. sodium hydrogen carbonate and chloroform. The combined chloroform extracts (3×200 ml) were evaporated yielding a light yellow solid material that was TLC pure. Yield: 24.55 g (100%)

Compound 5: Compound (4) (24.0 g) was suspended in 100 ml of acetic anhydride. The mixture was refluxed for 20 min which resulted in a homogenous dark solution. Acetic anhydride was evaporated on a Rotavapor and the oily residue was neutralized with saturated sodium hydrogen carbonate, followed by extraction with chloroform (3×200 ml). The chloroform phase was evaporated and the crude material was flash chromatographed using 2% ethanol/chloroform as a solvent. The pure fractions were evaporated yielding oil that was TLC and NMR pure. Yield: 19.55 g (69%).

Compound 6: Compound (5) (19 g, 60.5 mmole), was oxidized as described in Example 3. The crude, single spot on the TLC product was isolated after standard work up. Yield: 18.97 g (95%), oil.

Compound 7: Compound (6) (18.5 g, 56 mmole), was converted to product (7) in a synthesis analogous to the synthesis in Example 4. The neutralized, end-extracted product was evaporated and flash chromatographed using 2% ethanol/chloroform as a solvent. The pure fractions containing the product were combined and evaporated. Yield: 12.04 g (61%), oil.

Compound 8: Diacetate (7) (12.0 g, 34.1 mmole), was dissolved in 50 ml of ethanol. To this solution stirred at RT, sodium hydroxide 5 M, 20 ml was added at once. After 10 min, when the TLC test for the substrate was negative, the mixture was neutralized with citric acid, and partitioned between sat. sodium hydrogen carbonate and ethanol/chloroform 1:1. The extraction was repeated three times using 100 ml of organic solvent for each extraction. The combined extracts were evaporated and the residual mixture was flash chromatographed using finally 8% ethanol/chloroform as a solvent. The appropriate pure fractions were collected and evaporated. Yield: 4.75 g (52%), yellow solid.

Compound 9: To the dihydroxy compound (8) (2.7 g, 9.44 mmole), in 35 ml of dry dichloromethane, phosphorus tribromide (3.63 g, 1.26 ml, 13.41 mmole) was added and the mixture was refluxed for 15 min. The reaction mixture was neutralized with saturated sodium hydrogen carbonate and extracted with chloroform (3×50 ml). The combined extracts were concentrated and crystallized from ethyl acetate. Yield: 3.91 g (84%)—white crystals.

Compound 10: Compound (9) (3.27 g, 7.9 mmole) and iminodiacetic acid diethylester (5.78 g, 30.5 mmole), were coevaporated together with toluene and redissolved in dry acetonitrile (50 ml). Solid sodium carbonate (10 g) was added and the mixture was refluxed for 2 h, whereafter the salts were filtered out and the filtrate was evaporated. The residue was flash chromatographed and the fractions containing the product evaporated to dryness. To achieve material free from any co-chromatographed iminodiacetic acid diethylester, the oily product was triturated with petrolether (3×20 ml) which yielded material free from any contaminations. Yield: 5.09 g (80%), oil.

Compound 12: To the solution of compound (10) (4.8 g, 7.5 mmole) in 50 ml of ethanol, 10% palladium on carbon (100 mg) was added followed by sodium borohydride (378 mg, 10 mmole). The reaction mixture was stirred at RT for 5 min and partitioned between sat. sodium hydrogen carbonate and chloroform. The chloroform extracts (3×50 ml) were concentrated and flash chromatographed to give the reduced form of compound (10) (=compound (11)) as an oil after evaporation. Yield: 3.89 g (85%).

The reduced form of compound (10) (250 mg) in 20 ml of ethanol, was treated with 1 M sodium hydroxide (10 ml) at RT for 3 h. The product, (pure according to TLC, solvent system acetonitrile/water 4:1) was neutralized with 1 M hydrochloric acid and concentrated. To the residue dissolved in water (25 ml), europium chloride hexahydrate (60 mg) dissolved in 5 ml of water was added and the mixture was stirred for 30 min. The excess of europium salt was removed by raising the pH to 8.5 with saturated sodium carbonate solution and filtration of the precipitate. The clear solution was evaporated almost to dryness and (12) was precipitated by addition of 10 ml of acetone. The product was washed on the filter with acetone and dried.

Compound 13: To the amino chelate (12) (100 mg) dissolved in 5 ml of water and vigorously stirred, thiophosgene (80 μl) dissolved in 3 ml of chloroform was added at once and the mixture was stirred at RT for 1 h.

The water phase was separated, extracted with chloroform (3×3 ml) and concentrated to a volume of 0.5 ml. Addition of ethanol (10 ml) precipitated (13) quantitatively as white solid. The TLC (System Acetonitrile/H₂O 4:1) and fluorescence developing with acetonyl acetone/EtOH (1:20) showed only a single product being negative to a fluorescamine test for free amines.

Compounds 11 and 13 were employed in the preceding examples.

Preparation of amino functionalized polyacrylamide
(Scheme 1)

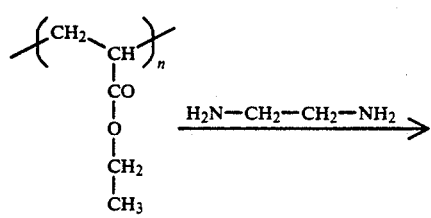

-continued
Preparation of amino functionalized polyacrylamide
(Scheme 1)

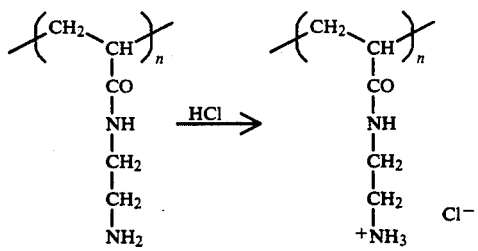

Preparation of carboxymethylated polyvinylamine (CMPVA)
(Scheme 2)

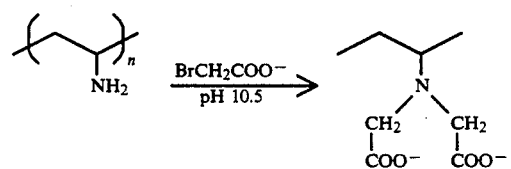

Preparation of functionalyzed polychelates by the polymerization of monomeric units (Scheme 3)

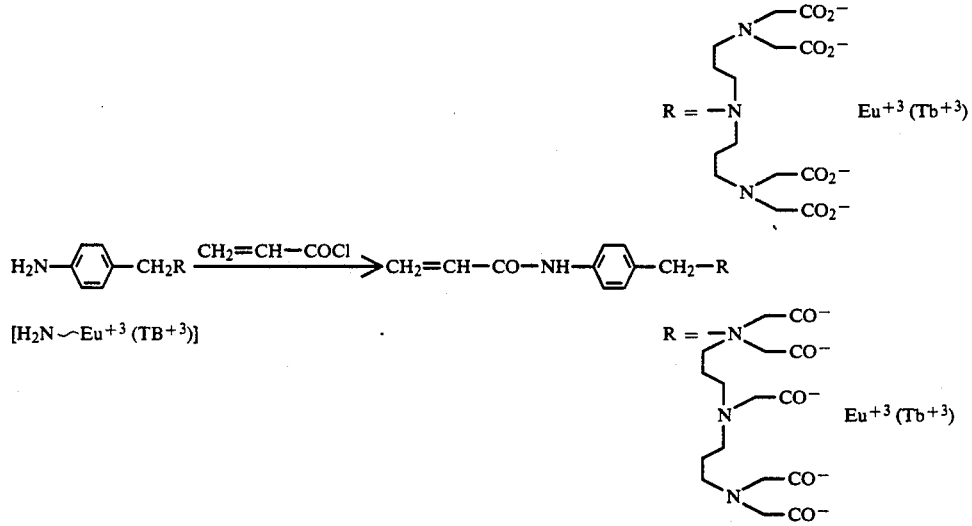

Synthesis of acrylamido chelates (Scheme 4)

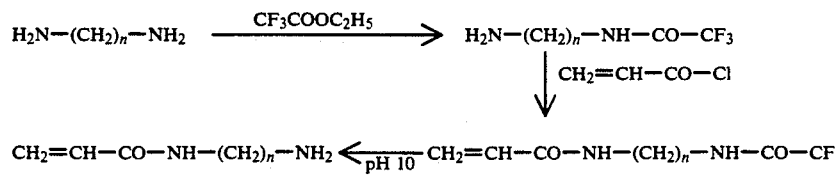

Synthesis of carboxymethylated polyvinylamine (CMPVA) having activated groups and chelate groups (scheme 5)
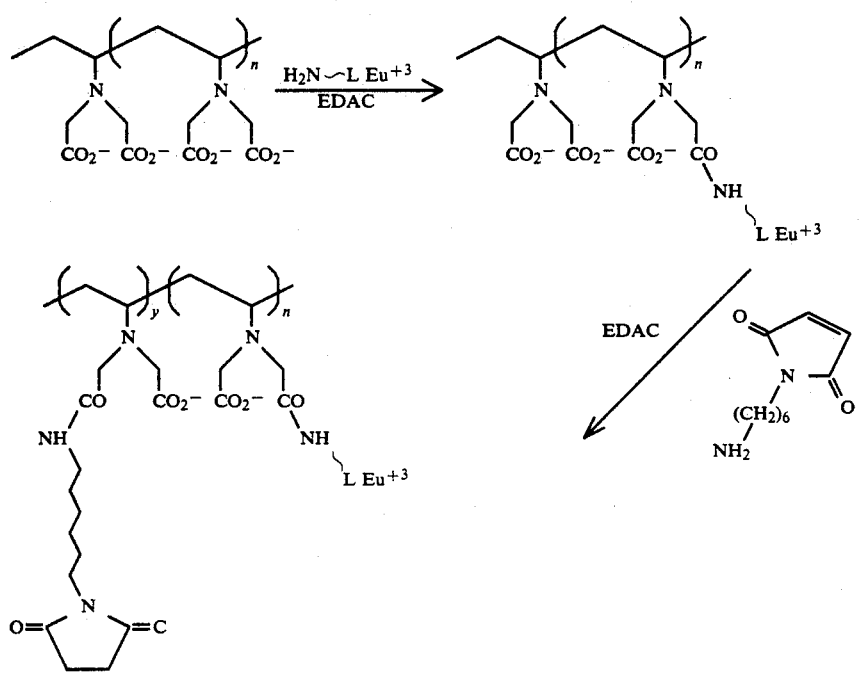
Application of polyvinylamine for the synthesis of activated polymeric chelate (Scheme 6)
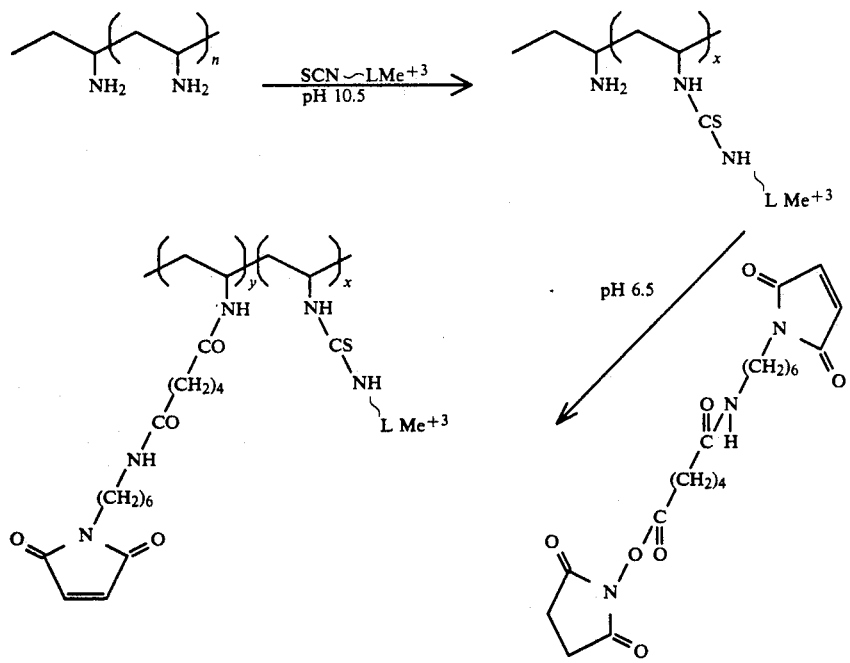
Construction of lanthanide-labelled oligodeoxribonucleic acid (Scheme 7)
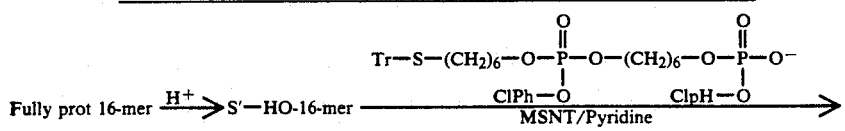

-continued
Construction of lanthanide-labelled oligodeoxribonucleic acid (Scheme 7)
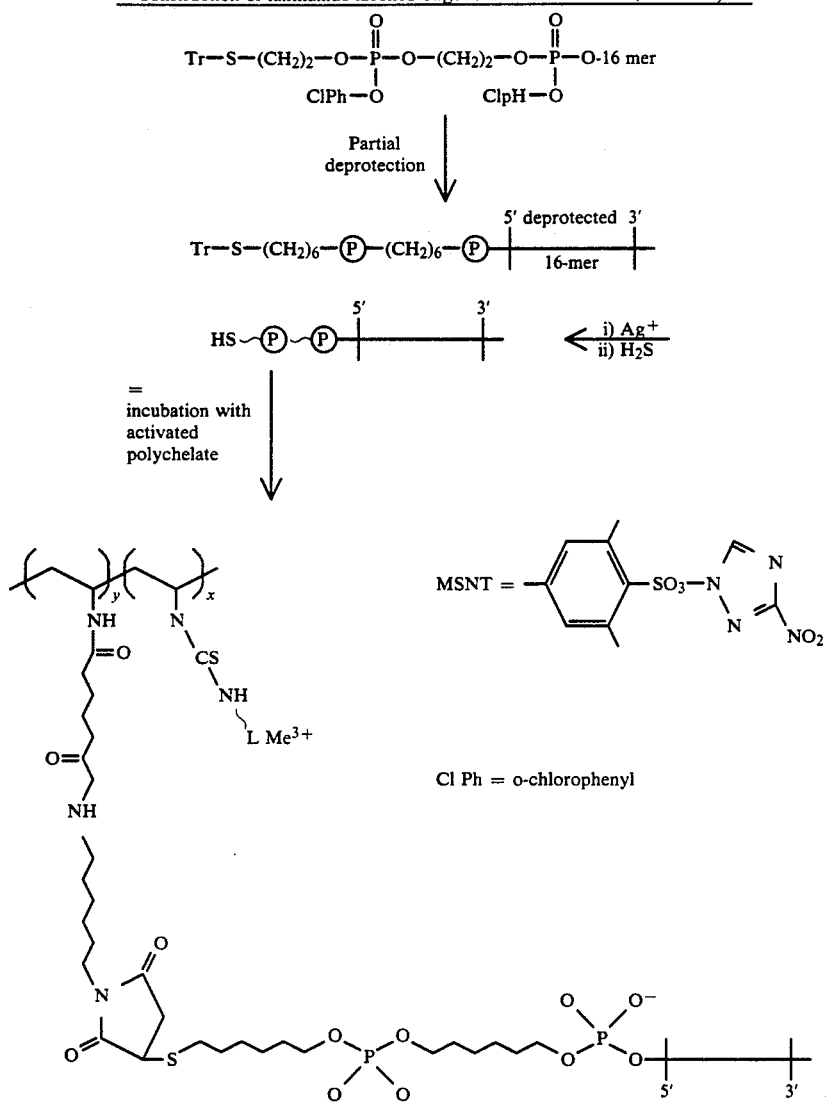

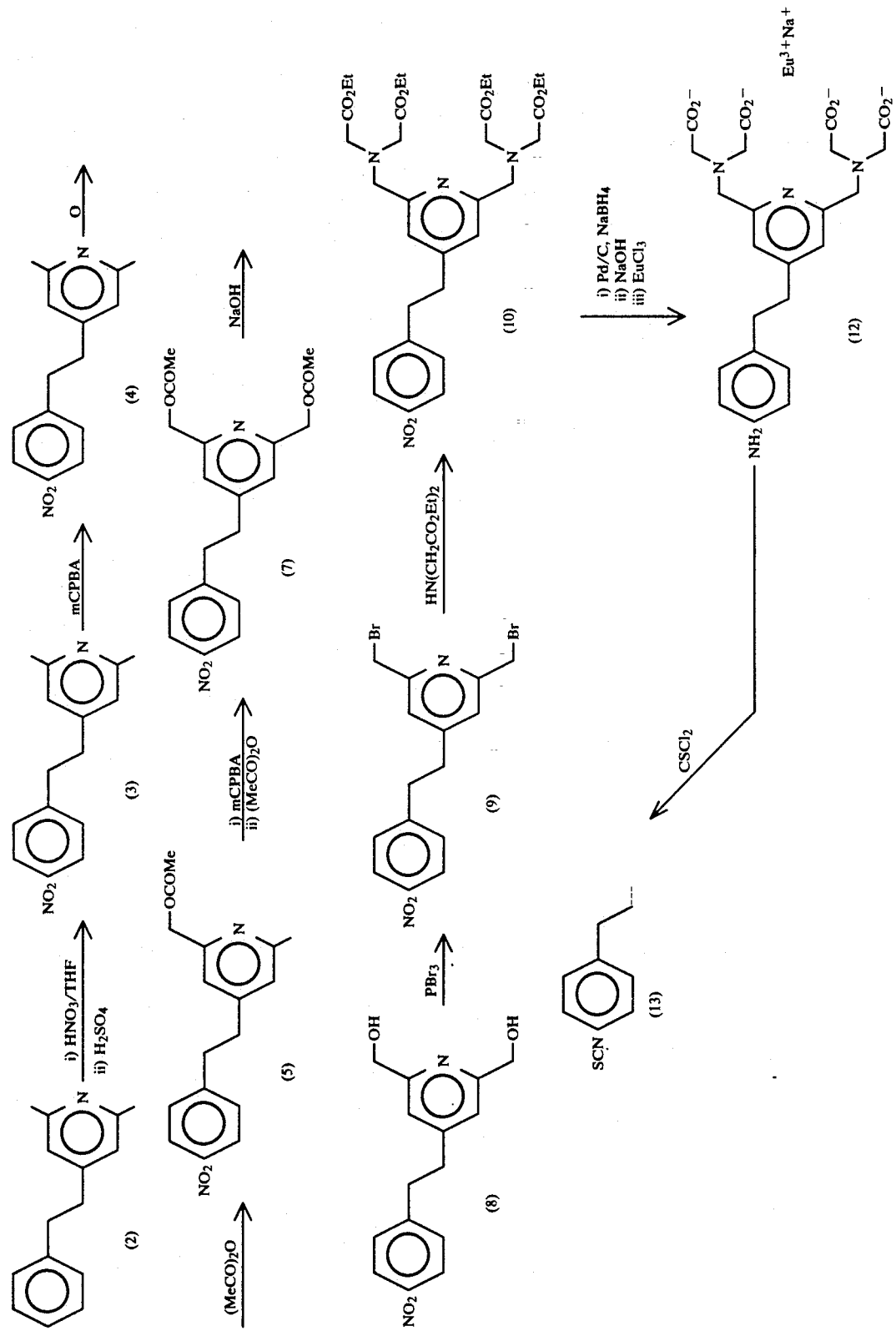

We claim:

1. A hybridization assay method for the detection of a nucleotide sequence of a nucleic acid in a sample, said method comprising the steps:
   (i) contacting under hybridization conditions the single stranded form of the sample nucleotide sequence with a single stranded nucleic acid probe, wherein:
      a) said probe has a nucleotide sequence complementary to the sequence to be detected,
      b) said probe has a water-soluble polymer bearing a plurality of chelating structures covalently linked to said polymer, wherein said water-soluble polymer is of non-nucleic acid structure and is covalently linked to said nucleotide sequence complementary to the sequence to be detected, and
      c) said probe has a plurality of rare earth metal ions that together with said chelating structures forms a plurality of chelate groups covalently bound to said water-soluble polymer, and said rare earth metal is selected from the group consisting of $Eu^{3+}$, $Tb^{3+}$, $Sm^{3+}$, and $Dy^{3+}$, wherein said probe and covalently bound chelate groups are stable under hybridization assay conditions:
   (ii) allowing a nucleotide sequence to be detected in said sample and the nucleotide sequence of said probe to form a double stranded nucleic acid; and
   (iii) detecting the formation of double stranded nucleic acid containing said probe by measuring the time-resolved fluorescence from the rare earth metal ions incorporated as a chelate in said double stranded nucleic acid.

2. The method of claim 1, wherein the said at least one metal ion is selected from the group consisting of $Eu^{3+}$ and $Tb^{3+}$.

3. The method of claim 1, wherein the water-soluble polymer is selected from the group of polymers having a plurality of OH— or amino groups.

4. The method of claim 3, wherein said water-soluble polymer having a plurality of OH groups is selected from the group consisting of polymers having alcohol, phenol and carboxy groups.

5. The method of claim 3, wherein the polymer is selected from the group of polymers consisting of polymers having a plurality of amino groups.

6. The method of claim 3, wherein the water-soluble polymer is selected from the group of polymers consisting of polyvinylamines, polyethyleneimines, polylysine, polysacharides, polyacrylamides, and derivatized forms of these polymers exhibiting the said plurality of OH—or amino groups.

7. The method of claim 1, wherein at least two nucleotide sequences complementary to the sequence to be detected are bound to the water-soluble polymer molecule.

8. The method of claim 1, wherein at least two water-soluble polymer molecules are bound to the nucleotide sequence complementary to the nucleotide sequence to be detected.

9. Nucleotide sequence to which a plurality of lanthanide chelate groups are bound covalently via a water-soluble polymer, said lanthanide being non-radioactive and selected from a group consisting of $Dy^{3+}$, $Sm^{3+}$, $Eu^{3+}$ and $Tb^{3+}$, preferably from group $Eu^{3+}$ and $Tb^{3+}$.

* * * * *